July 29, 1958 E. GODIN Plant Pat. 1,739
HIBISCUS PLANT
Filed Dec. 13, 1957
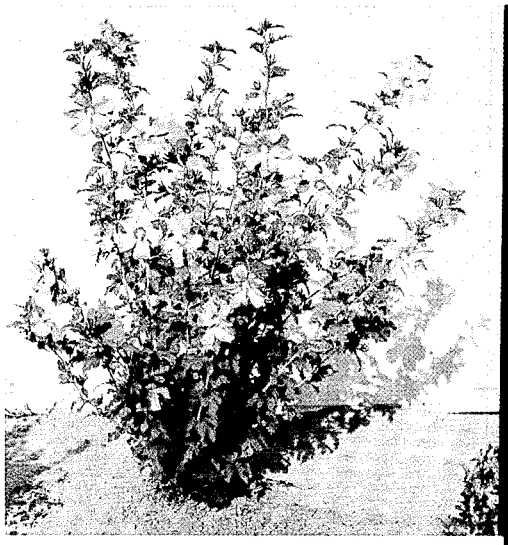
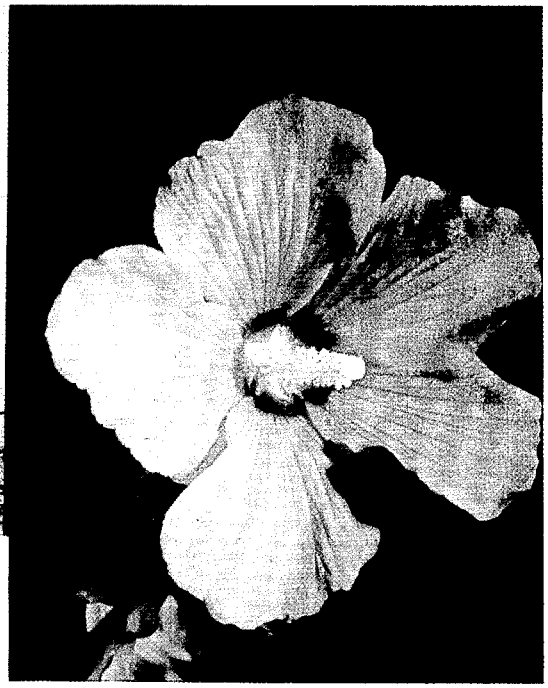
INVENTOR
Eugene Godin
BY Robb & Robb
ATTORNEYS United States Patent Office Plant Pat. 1,739
Patented July 29, 1958

1,739

HIBISCUS PLANT

Eugène Godin, Chatenay-Malabry, France, assignor, by mesne assignments, to Gulf Stream Products, Inc., Wachapreague, Va., a corporation of Virginia Application December 13, 1957, Serial No. 702,744

1 Claim. (Cl. 47—60)

The present invention relates to a new and distinct variety of hibiscus plant of the *Hibiscus syriacus* class, which was discovered and selected by me from a group of seedlings originating from a cross of *Hibiscus coelestis* with an unnamed and unpatented white seedling.

As the result of this breeding, the new variety is differentiated from its parents, as well as from all other varieties heretofore known of its class, by being a much stronger grower, and by having much larger flowers, said flowers being a clear Lobelia Blue color with a small Bishop Violet eye.

Asexual reproduction of the new variety by both cuttings and grafting, as performed by me at Chatenay-Malabry (Seine), France, shows that the foregoing characteristics and distinctions come true to form and are established and transmitted through succeeding propagations.

The accompanying drawing shows a typical specimen plant of the new variety, as well as a view of an individual flower on an enlarged scale, both views being depicted in color as nearly true as it is reasonably possible to make the same in a color illustration of this character.

The following is a detailed description of my new hibiscus variety, with color terminology in accordance with R. F. Wilson's Horticultural Colour Chart, except where general color terms of ordinary dictionary significance are obvious, as based upon observations made from specimens grown in France and at Wachapreague, Virginia, U. S. A.

*Plant*

Type: Shrub.

Class: *Hibiscus syriacus.*

Parentage: Seedling.

*Seed parent.*—*Hibiscus syriacus coelestis.*

*Pollen parent.*—An unnamed white seedling.

Propagation: Holds its distinguishing characteristics through succeeding propagations by both cuttings and grafting.

Growth habit: Strong; upright.

Foliage: 3-lobed; dentated; alternate; about 2″ long and about 1″ wide.

*Color.*—Upper side—Dark Spinach Green, Plate 0960. Under side—Fern Green, Plate 0862.

*Petiole.*—About ⅛″ long; hairy.

*Flower*

Petals: About 2½″ long; about 1¼″ wide; overlapping for ¾ or more of their length. Number—usually 5 or 6.

Flower form: Dish-shaped; irregular; ruffled and waved.

Flower size: About 5 to 5½″ in diameter.

Stamen tube: About 1⅛″ long; about 1/16″ diameter at the base. Color—white.

Stamen: Color—cream (equally distributed along the tube).

Stigma: 6-parted. Color—white.

Style: Color—white.

Pollen: Color—creamish.

Color of flowers: Inside—Lobelia Blue, Plate 41/2, lightly veined with Bishop Violet, Plate 34, with eye of Bishop Violet, Plate 34. Outside—Lobelia Blue, Plate 41/2.

Peduncle: About ⅝″ long; hairy; rugose; arranged at an angle of about 65° to stem after full development of the flower.

I claim:

A new and distinct variety of hibiscus plant of the *Hibiscus syriacus* class, substantially as herein shown and described, characterized particularly as to novelty by its strong habit of growth, its exceptionally large flowers, and the clear Lobelia Blue general color tonality of its flowers, said flowers having a small eye of Bishop Violet color.

No references cited.

UNITED STATES PATENT OFFICE

Certificate of Correction

Plant Pat. 1,739 July 29, 1958

Eugène Godin

It is hereby certified that error appears in the above numbered patent requiring correction and that the said Letters Patent should read as corrected below.

The present sheet of drawing should be cancelled and the sheet as shown below substituted therefor, as part of the Letters Patent:

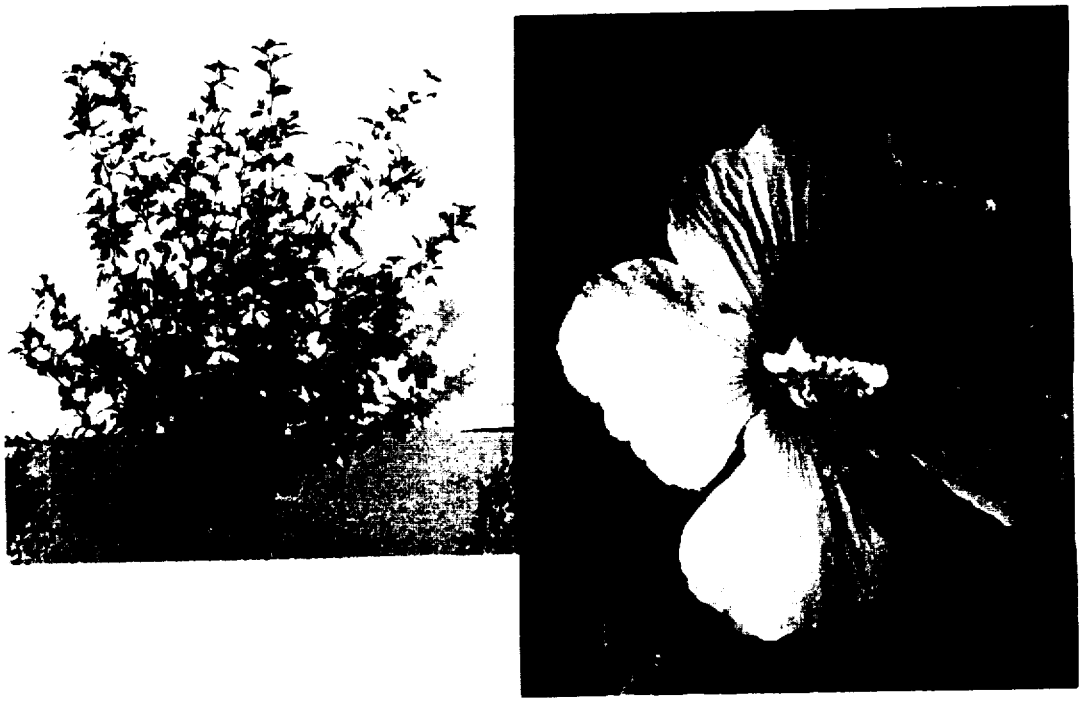

Signed and sealed this 21st day of October 1958.

[SEAL]

Attest:
KARL H. AXLINE,
*Attesting Officer.*

ROBERT C. WATSON,
*Commissioner of Patents.*